(12) United States Patent
Moloney (10) Patent No.: US 7,806,923 B2
(45) Date of Patent: Oct. 5, 2010

(54) SIDE BRANCH STENT HAVING A PROXIMAL SPLIT RING

(75) Inventor: Noreen Moloney, Moycullen (IE)

(73) Assignee: Medtronic Vascular, Inc., Santa Rosa, CA (US)

( * ) Notice: Subject to any disclaimer, the term of this patent is extended or adjusted under 35 U.S.C. 154(b) by 81 days.

(21) Appl. No.: 12/101,339

(22) Filed: Apr. 11, 2008

(65) Prior Publication Data
US 2009/0259293 A1 Oct. 15, 2009

(51) Int. Cl.
A61F 2/06 (2006.01)
(52) U.S. Cl. .................. 623/1.35; 623/1.15; 606/139
(58) Field of Classification Search .............. 606/139, 606/142, 151; 623/1.15, 1.35, 1.1, 1.16
See application file for complete search history.

(56) References Cited

U.S. PATENT DOCUMENTS

| | | | |
|---|---|---|---|
| 4,739,762 A | 4/1988 | Palmaz | |
| 5,133,732 A | 7/1992 | Wiktor | |
| 5,292,331 A | 3/1994 | Boneau | |
| 5,421,955 A | 6/1995 | Lau et al. | |
| 6,090,127 A | 7/2000 | Globerman | |
| 6,342,059 B1 * | 1/2002 | Chevillon et al. | ........... 606/139 |
| 2005/0222672 A1 | 10/2005 | Shmulewitz | |
| 2007/0032855 A1 | 2/2007 | Davidson et al. | |

* cited by examiner

*Primary Examiner*—David H Willse
*Assistant Examiner*—Matthew Schall (57) ABSTRACT

A side branch stent has a generally cylindrical body portion and a proximal split ring formed of a first semi-circular portion and a second semi-circular portion. The first semi-circular portion has a larger radius than the second semi-circular portion such that in a compressed configuration, the second semi-circular portion nests within the first semi-circular portion. Upon expansion of the side branch stent the two detached semi-circular portions expand to form a ring. The outer diameter of the proximal split ring, in both the compressed and expanded configurations, is larger than the outer diameter of the generally cylindrical body portion. The proximal split ring is used as a stopper or anchor which contacts the ostium of a vessel or the inner surface of a stent deployed in a main vessel of a bifurcated vessel in order to properly position the side branch stent in a side branch vessel.

21 Claims, 11 Drawing Sheets

SIDE BRANCH STENT HAVING A PROXIMAL SPLIT RING

FIELD OF THE INVENTION

The invention relates generally endoluminal prostheses, and more particularly to a stent intended for placement in a side branch vessel associated with a bifurcated or trifurcated vessel.

BACKGROUND OF THE INVENTION

Heart disease, specifically coronary artery disease, is a major cause of death, disability, and healthcare expense in the United States and other industrialized countries. A number of methods and devices for treating coronary heart disease have been developed, some of which are specifically designed to treat the complications resulting from atherosclerosis and other forms of coronary arterial narrowing.

One method for treating such conditions is percutaneous transluminal coronary angioplasty (PTCA). Generally, PTCA is a procedure that involves passing a balloon catheter over a guidewire to a stenosis with the aid of a guide catheter. The stenosis may be the result of a lesion such as a plaque or thrombus. The guidewire extends from a remote incision to the site of the stenosis, and typically across the lesion. The balloon catheter is passed over the guidewire, and ultimately positioned across the lesion. Once the balloon catheter is appropriately positioned across the lesion, e.g., under fluoroscopic guidance, the balloon is inflated to break-up the plaque of the stenosis to thereby increase the vessel cross-section. The balloon is then deflated and withdrawn over the guidewire into the guide catheter to be removed from the body of the patient. In many cases, a stent or other prosthesis must be implanted to provide permanent support for the vessel. Stents are typically constructed of a metal or polymer and are generally a hollow cylindrical shape. When such a device is to be implanted, a balloon catheter, typically carrying a stent on its balloon, is deployed to the site of the stenosis. The balloon and accompanying stent are positioned at the location of the stenosis, and the balloon is inflated to circumferentially expand and thereby implant the stent. Thereafter, the balloon is deflated and the catheter and the guidewire are withdrawn from the patient.

Although systems and techniques exist that work well in many cases, no technique is applicable to every case. For example, special methods exist for dilating lesions that occur in branched or bifurcated vessels. A bifurcation is an area of the vasculature where a main vessel is bifurcated into two or more branch vessels. It is not uncommon for stenotic lesions to form at such bifurcations. The stenotic lesions can affect only one of the vessels, i.e., either of the branch vessels or the main vessel, two of the vessels, or all three vessels.

Methods to treat bifurcated vessels seek to prevent the collapse or obstruction of the main and/or branch vessel(s) during the dilation of the vessel to be treated. Such methods include techniques for using double guidewires and sequential percutaneous transluminal coronary angioplasty (PTCA) with stenting or the "kissing balloon" and "kissing stent" techniques, which provide side branch protection. Administering PTCA and/or implanting a stent at a bifurcation in a body lumen poses further challenges for the effective treatment of stenoses in the lumen. For example, dilating a vessel at a bifurcation may cause narrowing of an adjacent branch of the vessel. In response to such a challenge, attempts to simultaneously dilate both branches of the bifurcated vessel have been pursued. These attempts include deploying more than one balloon, more than one prosthesis, a bifurcated prosthesis, or some combination of the foregoing. However, simultaneously deploying multiple and/or bifurcated balloons with or without endoluminal prostheses, hereinafter individually and collectively referred to as a bifurcated assembly, requires highly accurate placement of the assembly. Specifically, deploying a bifurcated assembly requires positioning a main body of the assembly within the trunk of the vessel adjacent the bifurcation, and then positioning the independent legs of the assembly into separately branching legs of the body lumen.

Implanting a stent at a bifurcation in a body lumen requires additional consideration of appropriate stent sizes due to the relative sizes of the main vessel and the branch vessels. Some branch vessels can have somewhat smaller diameter lumens than the main vessel from which they branch. In addition, some branch vessels can have lumens with somewhat different diameters from each other. Therefore, stents of different sizes may be needed for properly deploying a stent in each of the main and branch vessels. It would be desirable to allow a clinician to custom-select different combinations of stent sizes for deploying stents in main or branch vessels having different diameter lumens. Further, it would be desirable to allow for differential sizing of a side branch stent even after the main vessel stent is implanted.

Further, stent implantation may cause undesirable reactions such as restenosis, inflammation, infection, thrombosis, and proliferation of cell growth that occludes the passageway. These reactions are especially common when repairing a vessel affected by stenosis at the point at which the vessel originates, branching off from an adjoining vessel. This point of origin is referred to as the ostium of the vessel, which is prone to restenosis. A bulk of material (such as, for example, overlapping stent struts) often occurs at the ostium and acts as an initiation site for thrombus and/or restenosis. To assist in preventing these conditions, stents have been used with coatings to deliver drugs or other therapeutic agents at the site of the stent. However, it would be desirable to provide a side branch stent having a design or structure that allows for less turbulent blood flow at the ostium and thus minimizes undesirable reactions such as those listed above.

BRIEF SUMMARY OF THE INVENTION

Embodiments of the present invention are directed to an intraluminal stent device for placement in a side branch vessel associated with a bifurcated vessel. The stent device includes an expandable body portion having a generally cylindrical hollow shape with an outer diameter, the body portion having a proximal end and a distal end. The stent device also includes a split ring including a first semi-circular portion and a second semi-circular portion. The first semi-circular portion and the second semi-circular portion are attached to the proximal end of the body portion and are not attached to each other. The split ring is adapted to collapse to a first configuration during implantation and deploy to a second configuration after implantation. In the first configuration, the second semi-circular portion nests within the first semi-circular portion in order to achieve a low profile sufficient for delivery to the bifurcated vessel. In the second configuration, the second semi-circular portion and the first semi-circular portion expand to form a ring in order to properly position the stent device in the side branch vessel.

BRIEF DESCRIPTION OF DRAWINGS

The foregoing and other features and advantages of the invention will be apparent from the following description of the invention as illustrated in the accompanying drawings. The accompanying drawings, which are incorporated herein and form a part of the specification, further serve to explain the principles of the invention and to enable a person skilled in the pertinent art to make and use the invention. The drawings are not to scale.

DETAILED DESCRIPTION OF THE INVENTION

Specific embodiments of the present invention are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician.

The following detailed description is merely exemplary in nature and is not intended to limit the invention or the application and uses of the invention. Although the description of the invention is in the context of treatment of blood vessels such as the coronary, carotid and renal arteries, the invention may also be used in any other body passageways where it is deemed useful, including any body lumen or tubular tissue within the cardiac, coronary, renal, peripheral vascular, gastrointestinal, pulmonary, urinary and neurovascular systems and the brain. Furthermore, there is no intention to be bound by any expressed or implied theory presented in the preceding technical field, background, brief summary or the following detailed description.

Figure 1:
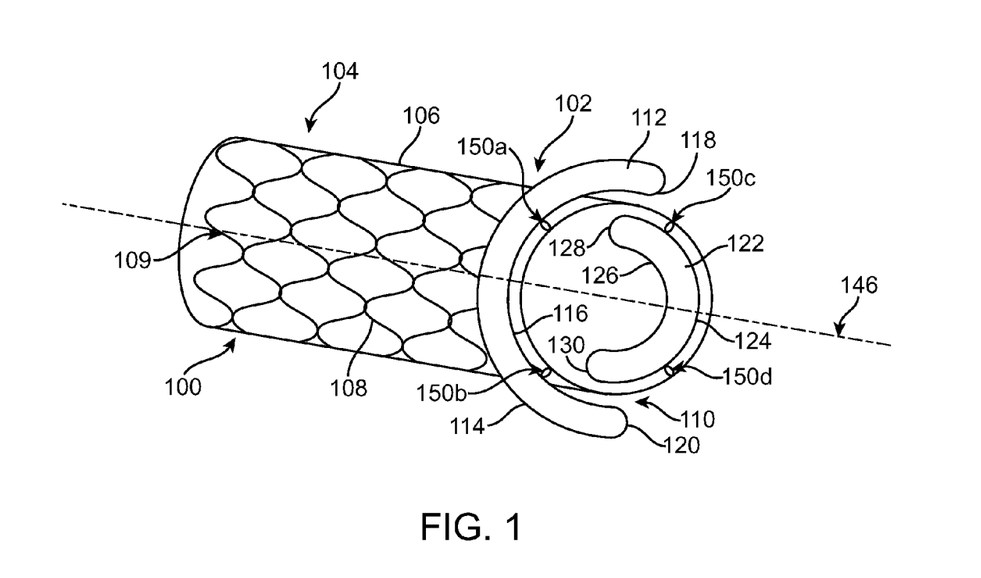
FIG. 1 is a perspective view of a side branch stent in accordance with an embodiment of the present invention.

FIG. 1 illustrates a side branch stent 100 intended for placement in a side branch vessel associated with a bifurcated or trifurcated vessel. Side branch stent 100 includes a generally cylindrical hollow body portion 106 extending between a proximal end 102 and a distal end 104. Body portion 106 is configured to fit into a side branch vessel. Side branch stent 100 also includes a split ring 110 at proximal end 104, which is configured to act as a stopper or anchor which contacts the ostium of a vessel or the inner surface of a stent deployed in a main vessel of a bifurcated or trifurcated vessel in order to properly position side branch stent 100 in a side branch vessel, as described in detail below.

According to embodiments of the present invention, body portion 106 may have a generally tubular or cylindrical expandable structure and may be circularly symmetric with respect to a central longitudinal axis. An outer diameter of body portion 106 in its expanded state may be approximately equal to or slightly larger than an inner diameter of a target side branch vessel. In one embodiment of the present invention, the outer diameter of body portion 106 may be substantially constant along the central longitudinal axis. In another embodiment, the outer diameter of body portion 106 may vary along the central longitudinal axis in order to improve positioning of side branch stent 100 with respect to the side branch vessel and/or to ease the insertion of side branch stent 100 into the side branch vessel. For example, body portion 106 may have a generally tapered or conical shape such that the outer diameter of body portion 106 may gradually increase or decrease along the central longitudinal axis.

Body portion 106 includes a plurality of stent struts 108 formed into a generally hollow cylindrical configuration. One configuration for stent struts 108 includes a plurality of undulating or wavelike bands 109 having straight segments and turns (i.e., alternating turns facing opposite longitudinal directions). Bands 109 are aligned on a common longitudinal axis to form a generally cylindrical body having a radial and longitudinal axis and are connected together to form body portion 106. As will be apparent to those of ordinary skill in the art, stent struts 108 may have any suitable pattern, such as for example, a cross-hatched pattern, mesh pattern, or a coiled pattern. Body portion 106 may be any stent body known in the art may that has a suitable generally cylindrical configuration such as the stents shown or described in U.S. Pat. No. 5,292,331 to Boneau, U.S. Pat. No. 6,090,127 to Globerman, U.S. Pat. No. 5,133,732 to Wiktor, U.S. Pat. No. 4,739,762 to Palmaz, and U.S. Pat. No. 5,421,955 to Lau, which are incorporated by reference herein in their entirety.

Proximal split ring 110 of side branch stent 100 consists of two detached semi-circular portions, a first semi-circular portion 112 and a second semi-circular portion 122. The first and second semi-circular portions 112, 122 are detached in that they are not attached to each other, but are each attached to body portion 106 of side branch stent 100. First semi-circular portion 112 has a semi-circular shape having an outer peripheral surface 114, an inner surface 116, a first end 118 and a second end 120. Second semi-circular portion 122 has a semi-circular shape having an outer peripheral surface 124, an inner surface 126, a first end 128 and a second end 130. In one embodiment, first semi-circular portion 112 has a larger radius than second semi-circular portion 122, the radius being taken from the center of a circle that would include the respective semi-circular portion. In other words, if first semi-circular portion 112 and second semi-circular portion 122 were laid out flat in a straight line, first semi-circular portion 112 would be longer or have a length greater than that of second semi-circular portion 122.

Figure 2:
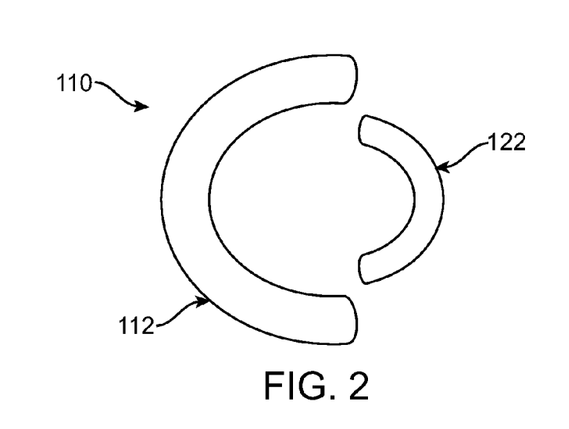
FIG. 2 is a front view of a proximal spit ring in a compressed or crimped configuration in accordance with an embodiment of the present invention.
Figure 3:
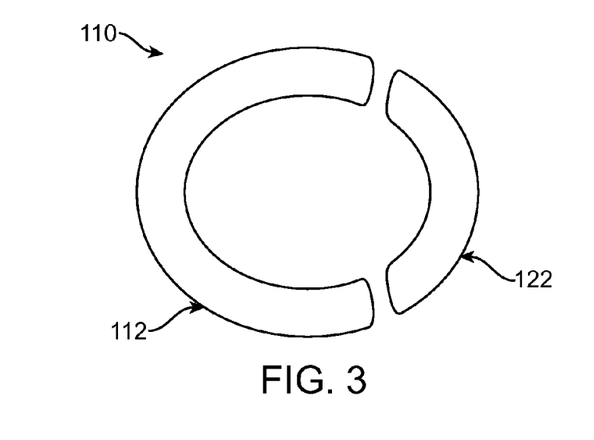
FIG. 3 is a front view of the proximal spit ring of FIG. 2 in an expanded or deployed configuration.

As shown in FIGS. 1-3, in one embodiment of the present invention, each semi-circular portion 112, 122 of proximal split ring 110 is a one-piece solid structure oriented substantially orthogonal to a central longitudinal axis 146 as viewed from proximal split ring 110 looking into body portion 106. Outer surfaces 114, 124 of semi-circular portions 112, 122, respectively, are smooth such that when positioned at the target bifurcated vessel as described in more detailed below, the smooth outer surfaces 114, 124 allow for less turbulent flow of blood at the ostium and thus minimize undesirable reactions such as restenosis, inflammation, infection, thrombosis, and proliferation of cell growth that occludes the passageway. In addition, a one-piece solid structure avoids overlapping of stent struts and thus a bulk of material that often occurs at the ostium and thus avoids creating an area prone to thrombus and/or restenosis.

Figure 4:
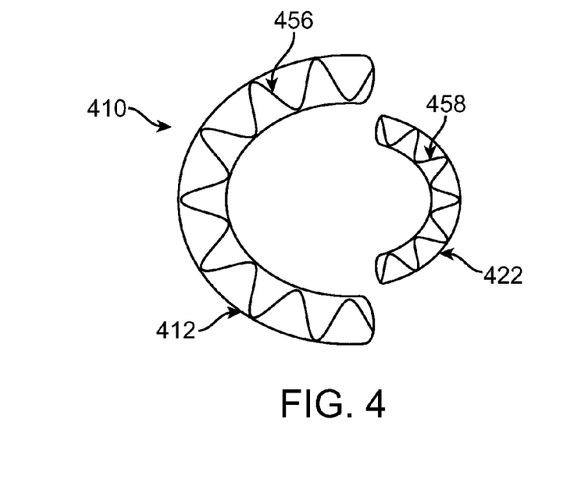
FIG. 4 is a front view of a proximal spit ring in a compressed or crimped configuration in accordance with another embodiment of the present invention.
Figure 5:
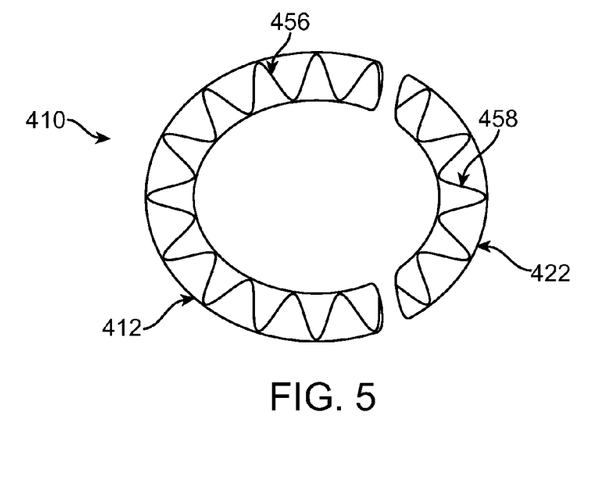
FIG. 5 is a front view of the proximal spit ring of FIG. 4 in an expanded or deployed configuration.

As shown in FIGS. 4-5, in another embodiment of the present invention, each semi-circular portion of the proximal split ring may include a single or double undulating stent strut oriented substantially orthogonal to the central longitudinal axis as viewed from the proximal split ring looking into body portion 106. For example, proximal split ring 410 consists of two detached semi-circular portions, a first semi-circular portion 412 and a second semi-circular portion 422. First semi-circular portion 412 includes a single undulating stent strut 456 oriented substantially orthogonal to the central longitudinal axis as viewed from proximal split ring 410 looking into body portion 106. Second semi-circular portion 422 includes a single undulating stent strut 458 oriented substantially orthogonal to the central longitudinal axis as viewed from proximal split ring 410 looking into body portion 106. Although described herein as a single continuous stent strut, it will be apparent to those of ordinary skill in the art that each semi-circular portion of the proximal split ring may alternatively be formed from a plurality of elements connected together and positioned about proximal end 102 of side branch stent 100.

Figure 6:
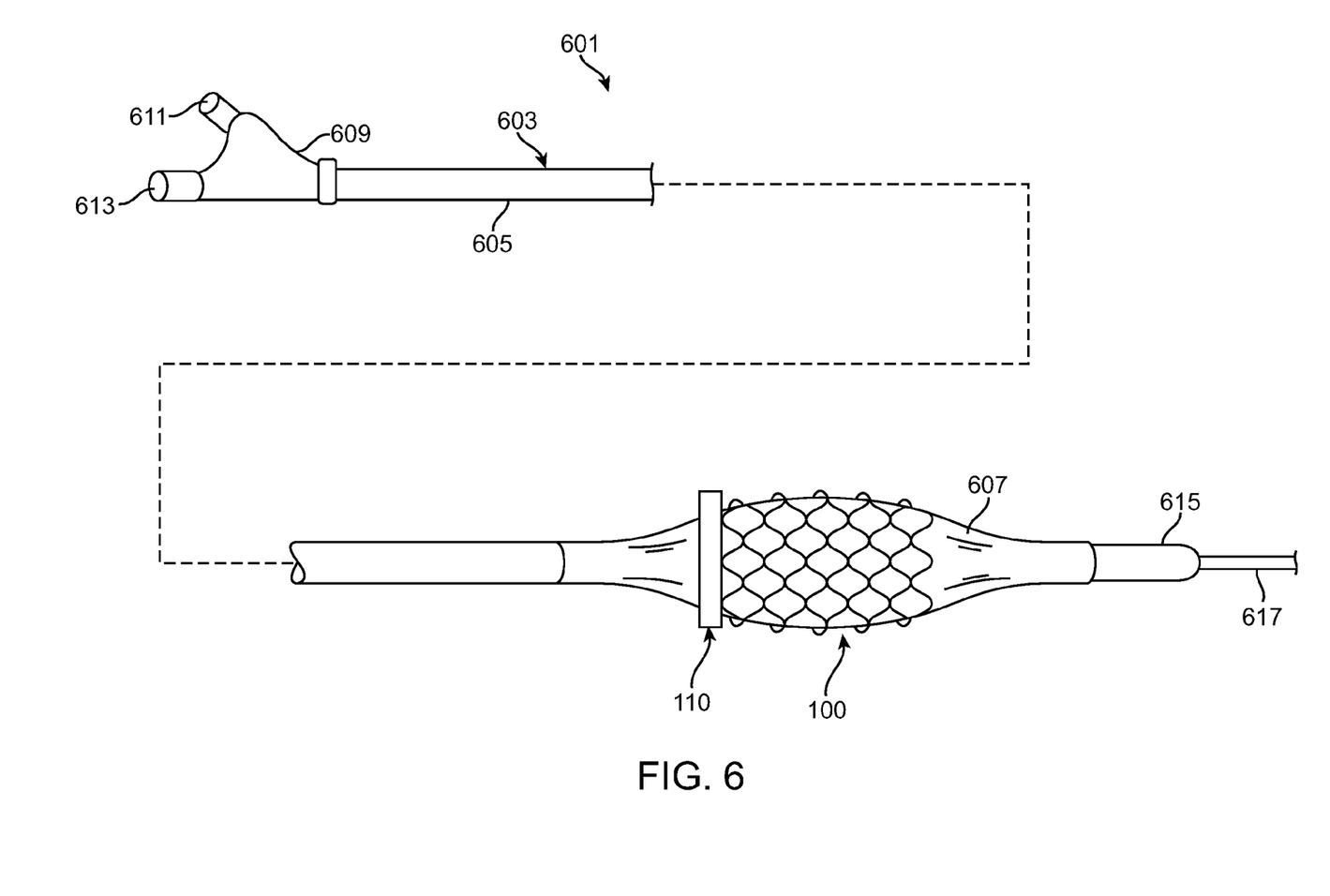
FIG. 6 is a side elevational view of a stent delivery system in accordance with an embodiment of the present invention.

Proximal split ring 110 is adapted to collapse to a first compressed or crimped configuration during implantation and deploy to a second expanded configuration after implantation. The first compressed or crimped configuration is illustrated in FIGS. 2, 4, and 6. As shown in FIGS. 2 and 4, in the first configuration, second semi-circular portion 122 nests within first semi-circular portion 112 to achieve a low delivery profile. When in the first compressed configuration, the outer diameter of proximal split ring 110 is greater than the outer diameter of body portion 106 so that the body portion 106 of side branch stent 100 may be inserted into the target side branch vessel and the larger diameter proximal split ring 110 will act as a stopper or anchor by contacting the inner surface of the main branch vessel and/or a stent located within the main branch vessel, as will be explained in more detail below.

Preferably, side branch stent 100 and proximal split ring 110 attached thereto is crimped onto a conventional balloon dilation catheter for delivery to a treatment site and expanded by the radial force of the balloon. Conventional balloon catheters that may be used in the present invention include any type of catheter known in the art, including over-the-wire catheters, rapid-exchange catheters, core wire catheters, and any other appropriate balloon catheters. For example, conventional balloon catheters such as those shown or described in U.S. Pat. Nos. 6,736,827; 6,554,795; 6,500,147; and 5,458,639, which are incorporated by reference herein in their entirety, may be used to deliver side branch stent 100 to a treatment site.

For example, FIG. 6 is an illustration of a stent delivery system 601 for tracking side branch stent 100 to the bifurcation target site in accordance with an embodiment of the present invention. Stent delivery system 601 includes a catheter 603 having a proximal shaft 605, a guidewire shaft 615, and a balloon 607. Proximal shaft 605 has a proximal end attached to a hub 609 and a distal end attached to a proximal end of balloon 607. Guidewire shaft 615 extends between hub 609 and a distal tip of catheter 603 through proximal shaft 605 and balloon 607. Hub 609 includes an inflation port 611 for coupling to a source of inflation fluid. Inflation port 611 fluidly communicates with balloon 607 via an inflation lumen (not shown) that extends through proximal shaft 606. In addition, hub 609 includes a guidewire port 613 that communicates with a guidewire lumen (not shown) of guidewire shaft 615 for receiving a guidewire 617 there through. As described herein, guidewire shaft 615 extends the entire length of catheter 603 in an over-the-wire configuration. However, as would be understood by one of ordinary skill in the art, guidewire shaft 615 may alternately extend only within the distal portion of catheter 603 in a rapid-exchange configuration. A side branch stent having a split proximal ring attached thereto formed in accordance with an embodiment of the present invention is positioned over balloon 607. If desired, a sheath (not shown) may be provided to surround side branch stent 100 and proximal split ring 110 attached thereto to facilitate tracking of the stent delivery system 601 over guidewire 617 through the vasculature to a site of a stenotic lesion.

Figure 7:
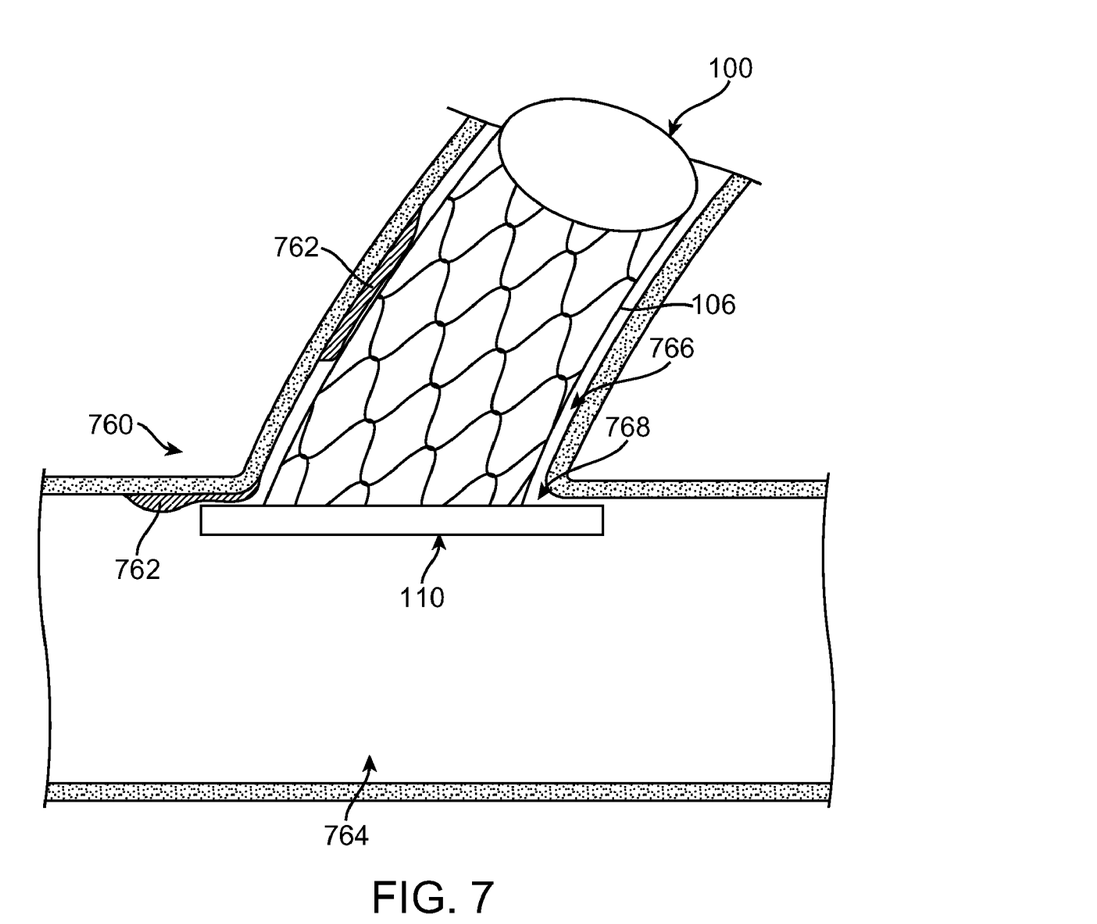
FIG. 7 is a sectional view of a side branch stent deployed in a bifurcated vessel in accordance with an embodiment of the present invention.

Deployment of balloon expandable side branch stent 100 is accomplished by threading catheter 603 through the vascular system of the patient until side branch stent 100 is located within a side branch vessel 766 of a bifurcated vessel 760. As shown in FIG. 7, the bifurcated vessel 760 includes a main vessel 764, an ostium 768, and side branch vessel 766. Bifurcated vessel 760 may include target tissue, for example, a lesion which may include plaque 762 obstructing the flow of blood through bifurcated vessel 760. The lesion may be located along at least part of main vessel 764, side branch vessel 766 and/or ostium 768 between side branch vessel 766 and main vessel 764. Once positioned, a source of inflation fluid is connected to inflation port 611 of hub 609 so that balloon 607 may be inflated to expand side branch stent 100 as is known to one of ordinary skill in the art. Balloon 607 of catheter 603 is inflated to an extent such that side branch stent 100 is expanded or deployed against the vascular wall of side branch vessel 766 to maintain the opening. Split proximal ring 110 will be seated within ostium 768, contacting the inside surface of main vessel 764 to anchor side branch stent 100 within side branch vessel 766. Stent deployment can be performed following treatments such as angioplasty, or during initial balloon dilation of the treatment site, which is referred to as primary stenting.

FIGS. 3, 5, and 7 illustrate the second deployed or expanded configuration of side branch stent 100. First semi-circular portion 112 and second semi-circular portion 122 are expanded or deployed by the conventional balloon catheter to form a ring or annular shape as illustrated in FIGS. 3, 5, and 7. The outer diameter of proximal split ring 110 in the second expanded or deployed configuration is greater than the outer diameter of proximal split ring 110 in the first compressed or crimped configuration. In addition, when in the second deployed configuration, the outer diameter of proximal split ring 110 is greater than the outer diameter of body portion 106 which is expanded or deployed against the vascular wall of side branch vessel 666 as described above.

Rather than being balloon-expandable as described above, one of ordinary skill in the art can appreciate that side branch stent 100 of the present invention can be adapted for any type of delivery method. For example, in another embodiment, side branch stent 100 may be self-expanding. Deployment of side branch stent 100 may be facilitated by utilizing shape memory characteristics of a material such as nickel-titanium (nitinol). More particularly, shape memory metals are a group of metallic compositions that have the ability to return to a defined shape or size when subjected to certain thermal or stress conditions. Shape memory metals are generally capable of being deformed at a relatively low temperature and, upon exposure to a relatively higher temperature, return to the defined shape or size they held prior to the deformation. This enables the stent to be inserted into the body in a deformed, smaller state so that it assumes its "remembered" larger shape once it is exposed to a higher temperature, i.e., body temperature or heated fluid, in vivo. Thus, self-expanding side branch stent 100 can have two states of size or shape, a contracted or compressed configuration sufficient for delivery to the treatment site and a deployed or expanded configuration having a generally cylindrical shape for contacting the vessel wall.

In another embodiment in which side branch stent 100 is self-expanding, body portion 106 and proximal split ring 100 may be constructed out of a spring-type or superelastic material such as nickel-titanium (nitinol), a nickel-tin alloy, a shape memory material, and other superelastic materials. A sheath (not shown) may be provided to surround and contain side branch stent 100 in a contracted or compressed position. Once side branch stent 100 is in position at the target side branch vessel, the sheath may be retracted, thus releasing side branch stent 100 to assume its expanded or deployed configuration.

Side branch stent 100 may be made from a variety of medical implantable materials, including, but not limited to, stainless steel, nickel-titanium (nitinol), cobalt-chromium, tantalum, ceramic, nickel, titanium, aluminum, polymeric materials, nickel-cobalt alloy such as MP35N, titanium ASTM F63-83 Grade 1, niobium, platinum, gold, silver, palladium, iridium, combinations of the above, and the like. In various embodiments of the present invention, side branch stent 100 may be made from a metallic material. Once implanted, the metallic stent provides artificial radial support to the wall tissue. Embodiments of the present invention also include side branch stent 100 being formed from a non-metallic material, such as a polymeric material.

In one embodiment of the present invention, proximal split ring 110 is of the same material as body portion 106. In another embodiment, proximal split ring 110 may be of a different material than body portion 106. For example, proximal split ring 110 may be formed from a more compliant material than body portion 106 to aid in conforming proximal split ring 110 to the shape of the ostium.

Side branch stent 100 may not always be visible to a physician viewing, for example, an X-ray fluoroscopy device while deploying and/or positioning side branch stent 100 into the bifurcated vessel. In one embodiment of the present invention, at least one marker (not shown) may be attached to side branch stent 100 at one or more predetermined locations. The marker may be formed of platinum or any other relatively heavy metal, which may be generally visible by X-ray fluoroscopy. For example, the marker may be attached to proximal end 102 of side branch stent 100 to allow a relatively high degree of accuracy for positioning side branch stent 100 into the bifurcated vessel, e.g., by aligning the marker with the ostial region.

In one embodiment of the present invention, at least a portion of side branch stent 100 may be coated with a therapeutic agent (not shown). Body portion 106 and/or proximal split ring 110 may be coated with a controlled-release polymer and/or drug, as known in the art, for reducing the probability of undesired side effects, e.g., restenosis. The therapeutic agent can be of the type that dissolves plaque material forming the stenosis or can be such as an antineoplastic agent, an antiproliferative agent, an antibiotic, an antithrombogenic agent, an anticoagulant, an antiplatelet agent, an anti-inflammatory agent, combinations of the above, and the like. Such drugs can include TPA, heparin, urokinase, or sirolimus, for example. Of course side branch stent 100 can be used for delivering any suitable medications to the walls of a body vessel.

Body portion 106 of side branch stent may be formed using any of a number of different methods. For example, body portion 106 may be formed by winding a wire or ribbon around a mandrel to form a strut pattern like those described above and then welding or otherwise mechanically connecting two ends thereof to form a circular band. A plurality of circular bands are subsequently connected together to form body portion 106. Alternatively, body portion 106 may be manufactured by machining tubing or solid stock material into toroid bands, and then bending the bands on a mandrel to form the pattern described above. A plurality of circular bands formed in this manner are subsequently connected together to form the longitudinal stent body. Laser or chemical etching or another method of cutting a desired shape out of a solid stock material or tubing may also be used to form body portion 106 of the present invention. In this manner, a plurality of circular bands may be formed connected together such that the stent body is a unitary structure. Further, body portion 106 of the present invention may be manufactured in any other method that would be apparent to one skilled in the art. The cross-sectional shape of side branch stent 100 may be circular, ellipsoidal, rectangular, hexagonal rectangular, square, or other polygon, although at present it is believed that circular or ellipsoidal may be preferable.

Proximal split ring 110 is connected to body portion 106 by a plurality of linking struts 150 such that expansion of proximal split ring 110 is not restricted. At least two linking struts 150 are required, one to connect first semi-circular portion 112 to body portion 106 and one to connect second semi-circular portion 122 to body portion 106. However, as will be apparent to those of ordinary skill in the art, any suitable number of linking struts 150 may be used to connect proximal split ring 110 to body portion 106. For example, as shown in FIG. 1, four linking struts may be used in total with two linking struts 150a, 150b connecting first semi-circular portion 112 to body portion 106 and two linking struts 150c, 150d connecting second semi-circular portion 122 to body portion 106. In another embodiment, a total of six, eight, or ten linking struts may be used to connect proximal split ring 110 to body portion 106. Linking struts 150 may be attached to body portion 106 and proximal split ring 110 by a form of welding, such as by resistance welding, friction welding, laser welding or another form of welding. Alternatively, linking struts 150 can be connected by soldering, by the addition of a connecting element, or by another mechanical method. Further, the stent having both body portion 106 and proximal split ring 110 may be formed pre-connected as a unitary structure, such as by laser cutting or etching the entire stent body from a hollow tube or sheet. Other connections or ways to connect body portion 106 and proximal split ring 110 would be apparent to one skilled in the art and are included herein.

Figure 8:
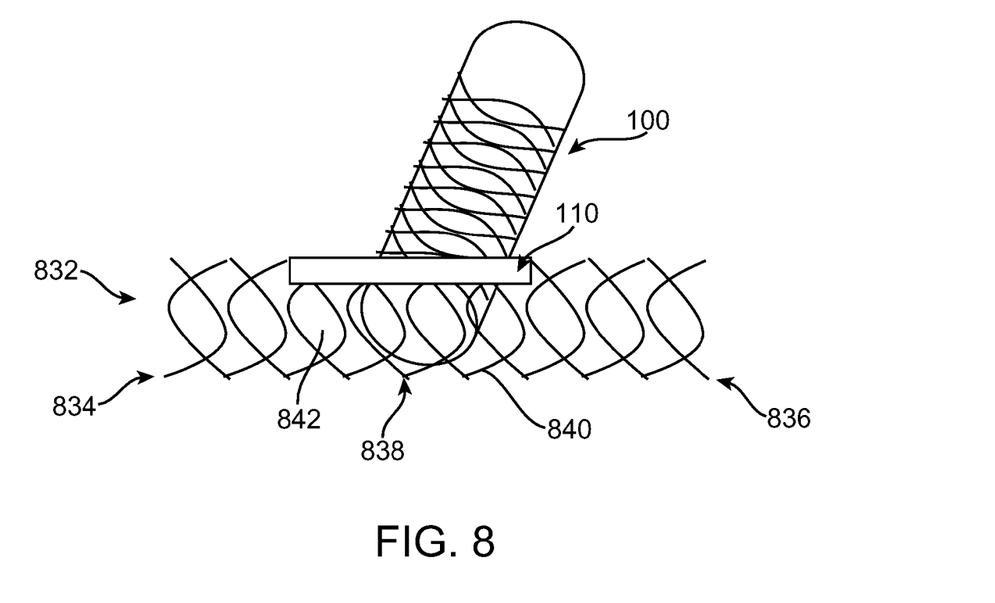
FIG. 8 is a perspective view of a side branch stent utilized in conjunction with a main vessel stent in accordance with an embodiment of the present invention.

Referring to FIG. 8, in one embodiment of the present invention, the side branch stent may be used in conjunction with a stent deployed in a main vessel of a bifurcation or trifurcation. A main vessel stent 832 includes a generally hollow cylindrical body portion 838 extending between a proximal end 834 and a distal end 836. Body portion 838 is configured to fit into a main vessel of a bifurcation. Proximal split ring of side branch stent 100 may contact an inner surface of main vessel stent 832 and thus acts as a stopper or anchor in order to properly position side branch stent 100 in a side branch vessel.

Figure 9:
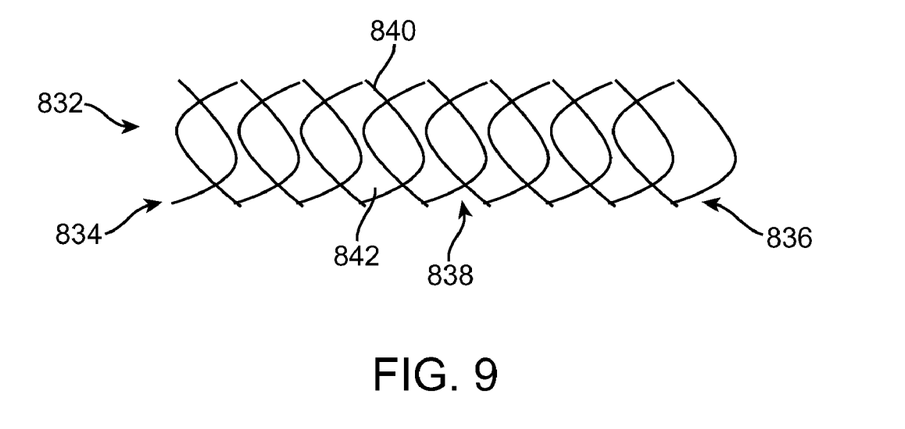
FIG. 9 is a perspective view of a main vessel stent in accordance with an embodiment of the present invention.

FIG. 9 illustrates main vessel stent 832 alone. Body portion 838 of main vessel stent 832 may have a generally tubular or cylindrical expandable structure and may be circularly symmetric with respect to a central longitudinal axis. When expanded, an outer diameter of body portion 838 may be approximately equal to or slightly larger than an inner diameter of a target main vessel of a bifurcation. Body portion 838 includes a plurality of stent struts 840 with cells or spaces 842 there between. Stent struts 840 are formed of a flexible material such that cells 842 may be manipulated in situ to allow insertion of body portion 106 of side branch stent 100 when main vessel stent 832 is deployed within the main vessel. The plurality of stent struts 840 are formed into a generally cylindrical configuration. One configuration for stent struts 840 are wavelike bands having straight segments and turns (i.e., alternating turns facing opposite longitudinal directions) aligned on a common longitudinal axis to form the generally cylindrical body and connected together to form body portion 838. As will be apparent to those of ordinary skill in the art, stent struts 840 may have any suitable pattern, such as for example, a cross-hatched pattern, mesh pattern, or a coiled pattern. Body portion 838 may be any stent body known in the art may that has a suitable generally cylindrical configuration such as the stents shown or described in U.S. Pat. No. 5,292,331 to Boneau, U.S. Pat. No. 6,090,127 to Globerman, U.S. Pat. No. 5,133,732 to Wiktor, U.S. Pat. No. 4,739,762 to Palmaz, and U.S. Pat. No. 5,421,955 to Lau, previously incorporated by reference herein in their entirety.

Figure 10:
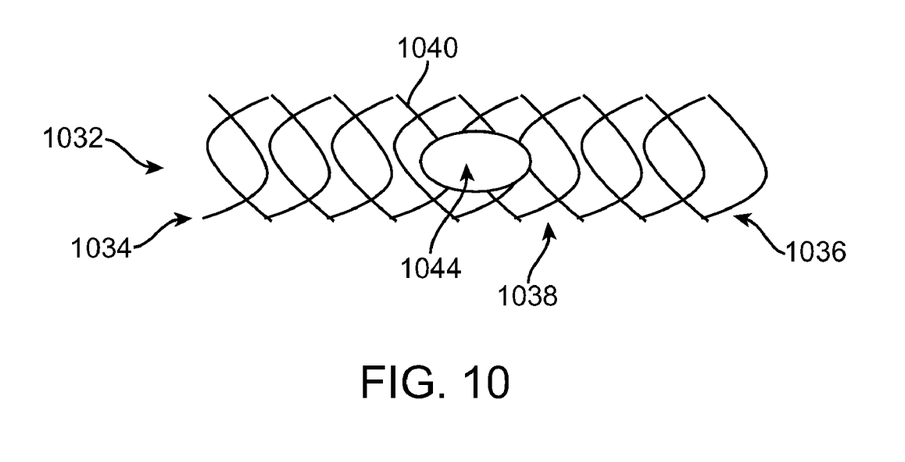
FIG. 10 is a perspective view of a main branch stent in accordance with another embodiment of the present invention.

FIG. 10 illustrates another embodiment of a main vessel stent 1032, including a generally cylindrical body portion 1038 extending between a proximal end 1034 and a distal end 1036. Body portion 1038 is configured to fit into a main vessel of a bifurcation. Body portion 1038 of main vessel stent 1032 may have a generally tubular or cylindrical expandable structure and may be circularly symmetric with respect to a central longitudinal axis. Body portion 1038 includes an opening 1044 which allows insertion of side branch stent 100 there through. Opening 1044 is positioned in the main vessel so that it is adjacent to the ostium of the side branch. Opening 1044 is of a sufficient size to allow insertion of body portion 106 of side branch stent 100 when main vessel stent 1032 is deployed within the main vessel. However, the size of opening 1044 is restricted so as not to allow proximal split ring 110 of side branch stent 100 to pass there through. In one embodiment, opening 1044 is circular but may also be other shapes so long as it allows insertion of body portion 106 of side branch stent 100. When expanded, an outer diameter of body portion 1038 may be approximately equal to or slightly larger than an inner diameter of a target main vessel of a bifurcation. Body portion 1038 includes a plurality of stent struts 1040 which are formed into a generally cylindrical configuration. Stent struts 1040 may have any suitable pattern, such as for example, undulating or wavelike bands, a cross-hatched pattern, mesh pattern, or a coiled. Stent struts 1040 are aligned on a common longitudinal axis to form a generally cylindrical body having a radial and longitudinal axis and are connected together to form body portion 1038.

The main vessel stent may be made from a variety of medical implantable materials, including, but not limited to, stainless steel, nickel-titanium (nitinol), cobalt-chromium, tantalum, ceramic, nickel, titanium, aluminum, polymeric materials, nickel-cobalt alloy such as MP35N, titanium ASTM F63-83 Grade 1, niobium, platinum, gold, silver, palladium, iridium, combinations of the above, and the like. In various embodiments of the present invention, the main vessel stent may be made from a metallic material. Once implanted, the metallic stent provides artificial radial support to the wall tissue. Embodiments of the present invention also include the main vessel stent being formed from a non-metallic material, such as a polymeric material. In one embodiment of the present invention, at least a portion of the main vessel stent may be coated with a therapeutic agent (not shown). The therapeutic agent can be of the type that dissolves plaque material forming the stenosis or can be such as an antineoplastic agent, an antiproliferative agent, an antibiotic, an antithrombogenic agent, an anticoagulant, an antiplatelet agent, an anti-inflammatory agent, combinations of the above, and the like.

The main vessel stent may be formed using any of a number of different methods. For example, the main vessel stent may be formed by winding a wire or ribbon around a mandrel to form a strut pattern like those described above and then welding or otherwise mechanically connecting two ends thereof to form a circular band. A plurality of circular bands are subsequently connected together to form the main vessel stent. Alternatively, the main vessel stent may be manufactured by machining tubing or solid stock material into toroid bands, and then bending the bands on a mandrel to form the pattern described above. A plurality of circular bands formed in this manner are subsequently connected together to form the longitudinal stent body. Laser or chemical etching or another method of cutting a desired shape out of a solid stock material or tubing may also be used to form the main vessel stent of the present invention. In this manner, a plurality of circular bands may be formed connected together such that the stent body is a unitary structure. Further, the main vessel stent of the present invention may be manufactured in any other method that would be apparent to one skilled in the art. The cross-sectional shape of the main vessel stent may be circular, ellipsoidal, rectangular, hexagonal rectangular, square, or other polygon, although at present it is believed that circular or ellipsoidal may be preferable.

Figure 11:
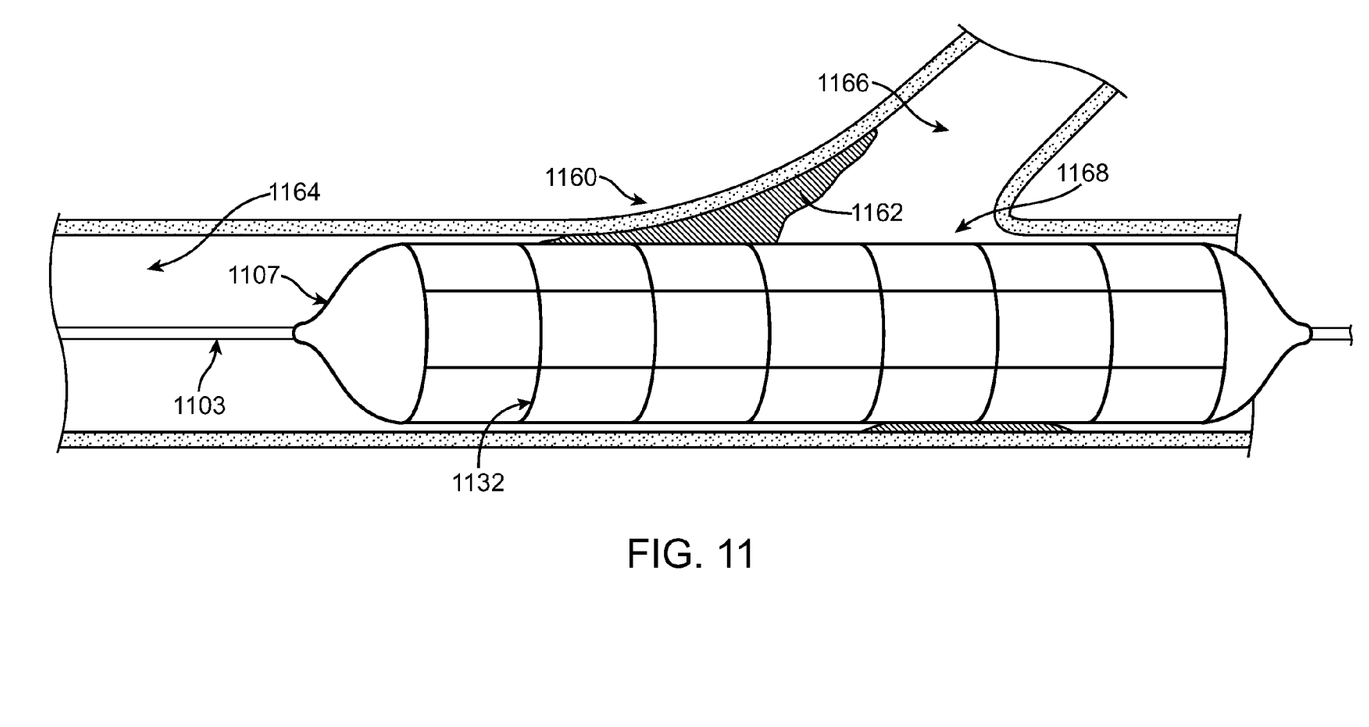
FIG. 11 is a sectional view of a main vessel stent deployed in a bifurcated vessel in accordance with an embodiment of the present invention.

FIGS. 11-15 illustrate a method of treating a bifurcated or trifurcated vessel using side branch stent 100 in conjunction with a main vessel stent 1132. FIG. 11 illustrates the main vessel stent 1132 deployed in a bifurcated vessel 1160. The bifurcated vessel 1160 includes a main vessel 1164, an ostium 1168, and a side branch vessel 1166. Bifurcated vessel 1160 may include target tissue, for example, a lesion which may include plaque 1162 obstructing the flow of blood through bifurcated vessel 1160. The lesion may be located along at least part of main vessel 1164, side branch vessel 1166 and/or ostium 1168 between side branch vessel 1166 and main vessel 1164. The main vessel stent 1132 may be balloon expandable or self-expandable, as described above with relation to side branch stent 100. For example, if the main vessel stent 1132 is balloon expandable, deployment of main vessel stent 1132 is accomplished by threading a balloon catheter 1103 through the vascular system of the patient until main vessel stent 1132 is located at a predetermined treatment site. Once positioned, balloon 1107 of catheter 1103 is inflated to expand main vessel stent 1132 against the vascular wall to maintain the opening. Stent deployment can be performed following treatments such as angioplasty, or during initial balloon dilation of the treatment site, which is referred to as primary stenting. Deployment of the main vessel stent may alternatively be accomplished by forming the main vessel stent of a self-expanding material such as a shape memory material or a superelastic material as described above with relation to side branch stent 100. Any of the main vessel stents described in the above embodiments, or similar main vessel stents, may be used.

Figure 12:
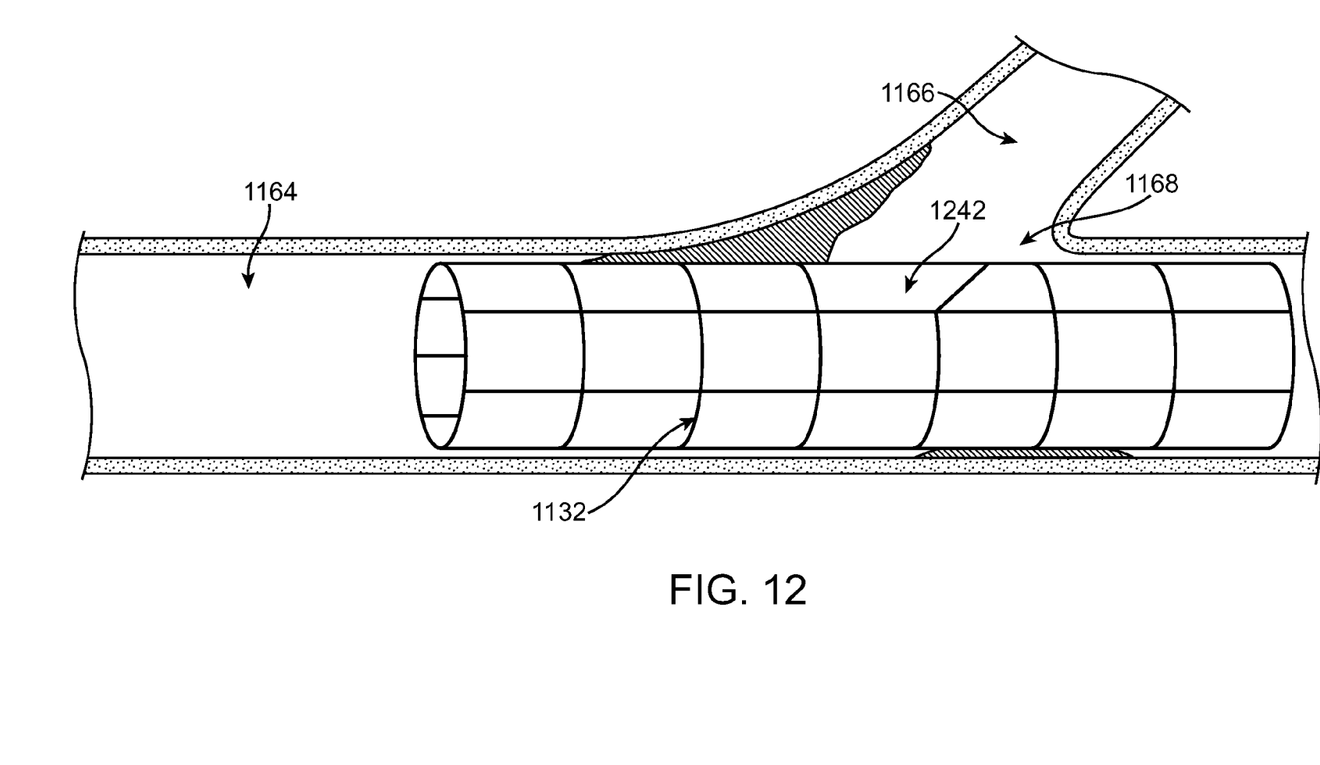
FIG. 12 is a sectional view of a main vessel stent having an expanded cell adjacent to the ostium in a bifurcated vessel in accordance with an embodiment of the present invention.

As shown in FIG. 12, once deployed in main vessel 1164, a cell 1242 (that is, the space between the struts of the main vessel stent) adjacent to ostium 1168 of the side branch 1166 is expanded in situ. Cell 1242 may be expanded by feeding a guidewire through cell 1242 and into the side branch, and inflating a balloon of a balloon catheter to open cell 1242 to the appropriate diameter. The balloon catheter for expanding cell 1242 may be the balloon catheter which delivered deployed main vessel stent 1132 if deemed appropriate by the operator, or alternatively may be a separate balloon catheter having a balloon of an appropriate diameter. Cell 1242 is expanded to the extent that the body portion of a side branch stent may pass there through but not expanded enough to allow passage of the proximal split ring of the side branch stent. If the main vessel stent includes an opening formed within main vessel stent's cylindrical body such as that described in relation to FIG. 10, the opening would be aligned with ostium 1168 to allow insertion of the side branch stent's body portion rather than expanding cell 1242.

Figure 13:
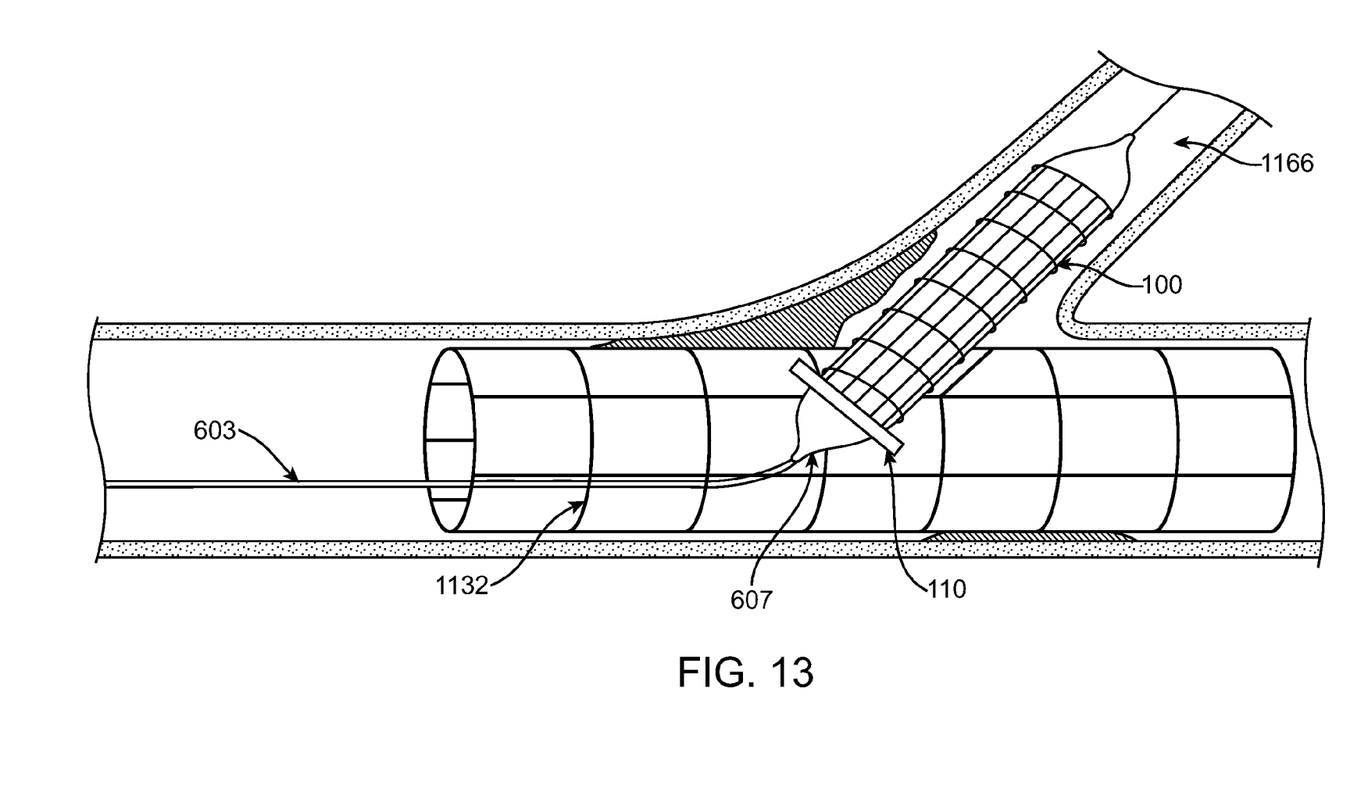
FIG. 13 is a sectional view of a side branch stent being inserted through a main vessel stent deployed in a bifurcated vessel in accordance with an embodiment of the present invention.
Figure 14:
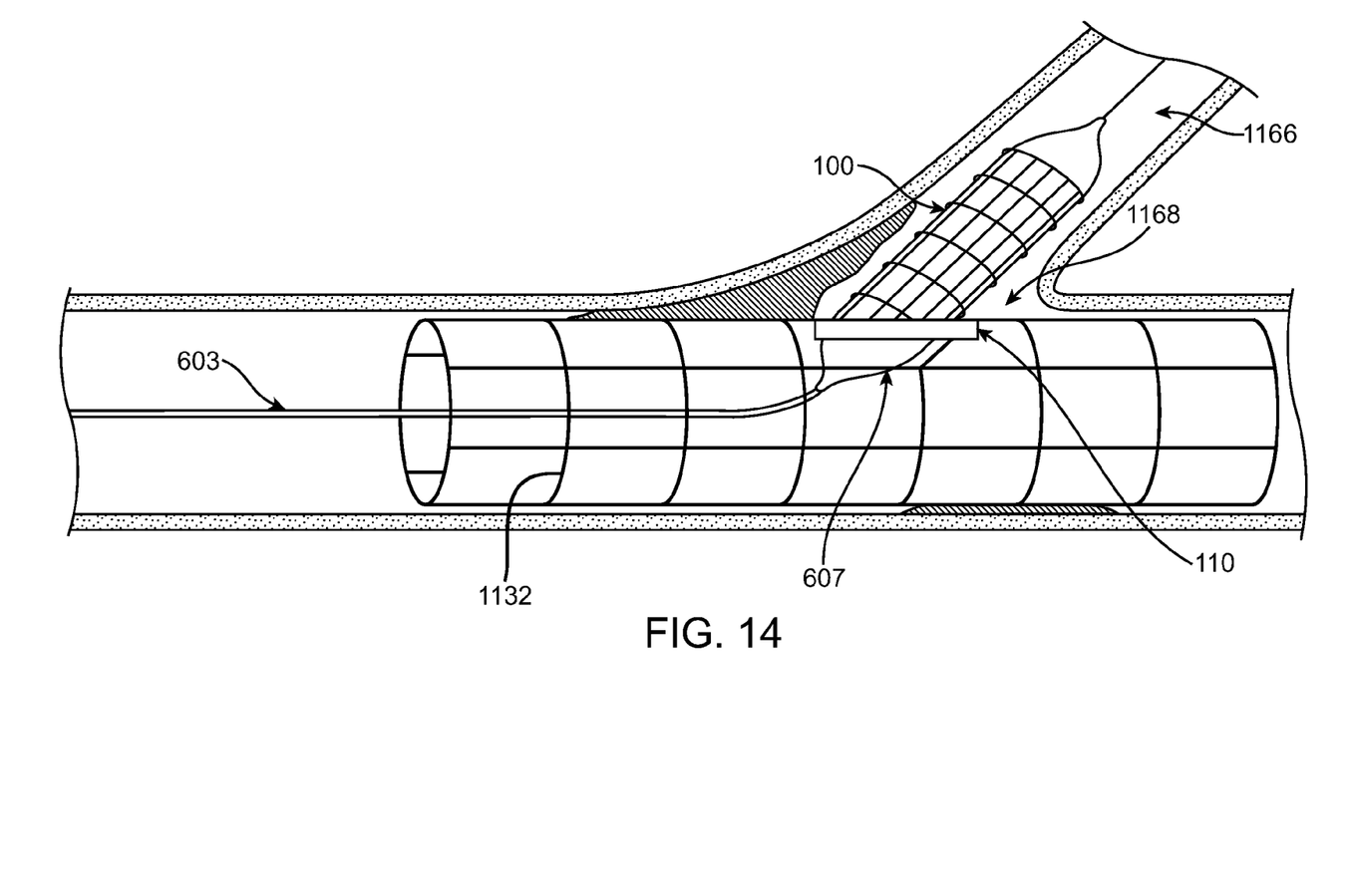
FIG. 14 is a sectional view of a side branch stent positioned within a side branch vessel in accordance with an embodiment of the present invention.

Once main branch stent is deployed and properly positioned at the bifurcation, side branch stent 100 is inserted into the vasculature while contracted into its compressed or crimped configuration. FIG. 13 illustrates side branch stent inserted through the deployed main vessel stent 1132. Side branch stent 100 is then inserted into the target side branch vessel 1166 through the expanded cell 1242 of the main branch stent 1132 until body portion 106 of side branch stent 100 is positioned within side branch vessel 1166. As shown in FIG. 14, proximal split ring 110 of side branch stent 100 acts as a stopper or anchor by contacting the inner surface of main branch stent 1132. As described above with respect to FIG. 6, positioning of side branch stent 100 is accomplished by threading catheter 603 with side branch stent 100 loaded onto balloon 607 at the distal end thereof through the vascular system of the patient until side branch stent 100 is located within side branch vessel 1166.

Figure 15:
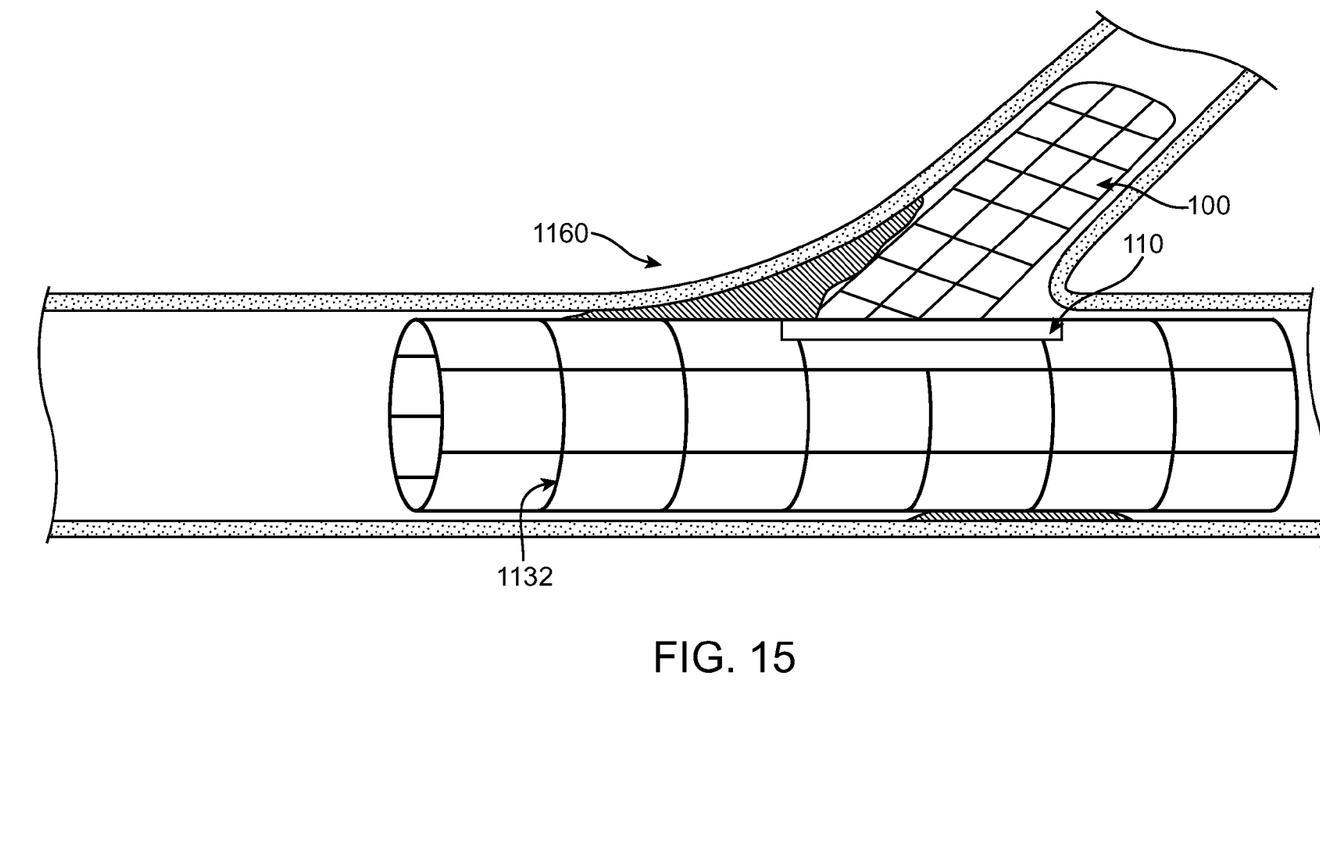
FIG. 15 is a sectional view of a side branch stent deployed within a side branch vessel in accordance with an embodiment of the present invention.

Once properly positioned within side branch vessel 1166, side branch stent 100 is then deployed. Side vessel stent may be balloon expandable or self-expandable, as described above. For example, if side branch stent 100 is balloon expandable, deployment is accomplished by inflating balloon 607 of catheter 603 to expand side branch stent 100 against the vascular wall to maintain the opening. Balloon 607 can be partially retracted to facilitate a second inflation at proximal split ring 110 to ensure that proximal split ring 110 and main vessel stent 132 are adequately expanded at ostium 1166 of bifurcated vessel 1160. Deployment of the side branch stent may alternatively be accomplished by forming the side branch stent of a self-expanding material such as a shape memory material or a superelastic material as described above. If side branch stent 100 is self-expanding, a sheath (not shown) may be provided to surround and contain the side branch stent 100 in a contracted or compressed position. Once side branch stent 100 is in position at the target side branch vessel, the sheath may be retracted, thus releasing side branch stent 100 and proximal split ring 110 to assume the expanded or deployed configuration. FIG. 15 illustrates side branch stent 100 and main vessel stent 1132 deployed within bifurcation 1160.

As shown in FIGS. 11-15, side branch stent 100 is implanted and deployed independently from main vessel stent 1132. Accordingly, a clinician may custom select an appropriate stent size for side branch stent 100 if side branch vessel 1166 is of a different lumen diameter than main vessel 1164. Such differential sizing of side branch stent 100 may occur even after main vessel stent 1132 is implanted.

While various embodiments according to the present invention have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. An intraluminal stent device for placement in a side branch vessel associated with a bifurcated vessel, comprising:

an expandable body portion having a generally cylindrical hollow shape having a proximal end and a distal end; and a split ring including a first semi-circular portion and a second semi-circular portion, wherein the first semi-circular portion and the second semi-circular portion are attached to the proximal end of the body portion and are not attached to each other, wherein the stent device includes a first unexpanded configuration and second expanded configuration, wherein in the first unexpanded configuration the body portion has a first body portion outer diameter and the split ring has a first split ring outer diameter, and wherein in the second expanded configuration the body portion has a second body portion outer diameter larger than the first body portion outer diameter and the split ring has a second split ring outer diameter larger than the first split ring outer diameter, wherein the first split ring outer diameter is larger than the first body portion outer diameter, and wherein the second semi-circular portion nests within the first semi-circular portion in the first unexpanded configuration.

2. The intraluminal stent device of claim 1, wherein the first semi-circular portion has a larger radius than the second semi-circular portion.

3. The intraluminal stent device of claim 1, wherein the second split ring outer diameter is larger than the second body portion outer diameter.

4. The intraluminal stent device of claim 1, wherein the split ring in the second configuration is configured to contact the ostium of the bifurcated vessel.

5. The intraluminal stent device of claim 1, wherein each of the first semi-circular portion and the second semi-circular portion are a solid one-piece structure oriented substantially orthogonal to a central longitudinal axis of the body portion.

6. The intraluminal stent device of claim 5, wherein the solid one-piece construction has a smooth outer surface.

7. The intraluminal stent device of claim 1, wherein each of the first semi-circular portion and the second semi-circular portion is formed from a single undulating stent strut oriented substantially orthogonal to a central longitudinal axis of the body portion.

8. The intraluminal stent device of claim 1, wherein the body portion of the stent device is formed of a plurality of undulating bands connected together and having a common longitudinal axis.

9. The intraluminal stent device of claim 1, wherein the split ring is connected to the body portion via a plurality of linking struts.

10. The intraluminal stent device of claim 9, wherein the plurality of linking struts consist of four linking struts.

11. An intraluminal stent system for placement in a bifurcated vessel, comprising:
    a first stent having a generally cylindrical hollow shape configured for placement in a main vessel of the bifurcated vessel, the first stent having an inner surface; and
    a second stent configured for placement in a side branch vessel of the bifurcated vessel, the second stent including an expandable body portion having a generally cylindrical hollow shape with a proximal end and a distal end, and a split ring including a first semi-circular portion and a second semi-circular portion with both portions being attached to the proximal end of the body portion and not attached to each other,
    wherein the second stent includes a first unexpanded configuration and second expanded configuration, wherein in the first unexpanded configuration the body portion has a first body portion outer diameter and the split ring has a first split ring outer diameter, and wherein in the second expanded configuration the body portion has a second body portion outer diameter larger than the first body portion outer diameter and the split ring has a second split ring outer diameter larger than the first split ring outer diameter,
    wherein the first split ring outer diameter is larger than the first body portion outer diameter, and
    wherein the second semi-circular portion nests within the first semi-circular portion in the first unexpanded configuration.

12. The intraluminal stent system of claim 11, wherein the first stent includes a plurality of struts with cells or spaces there between, the plurality of struts being formed of a flexible material such that the cells may be manipulated in situ to allow insertion of the body portion of the second stent.

13. The intraluminal stent system of claim 11, wherein the first stent includes a plurality of struts and an opening formed therein, the opening being sized to allow insertion of the body portion of the second stent therethrough in the first unexpanded configuration and being sized to prevent insertion of the split ring therethrough in the first unexpanded configuration.

14. The intraluminal stent system of claim 11, wherein the first semi-circular portion has a larger radius than the second semi-circular portion.

15. The intraluminal stent system of claim 11, wherein the second split ring outer diameter is larger than the second body portion outer diameter.

16. The intraluminal stent system of claim 11, wherein each of the first semi-circular portion and the second semi-circular portion is a solid one-piece structure oriented substantially orthogonal to a central longitudinal axis of the body portion.

17. The intraluminal stent system of claim 11, wherein each of the first semi-circular portion and the second semi-circular portion is formed from a single undulating stent strut oriented substantially orthogonal to a central longitudinal axis of the body portion.

18. The intraluminal stent system of claim 11, wherein the first stent includes a plurality of struts and an opening formed therein, the opening having a diameter larger than the first body portion outer diameter and smaller than the first split ring outer diameter.

19. The intraluminal stent system of claim 11, wherein the split ring contacts the inner surface of the first stent in the first unexpanded configuration and the second expanded configuration.

20. The intraluminal stent system of claim 11, wherein an inner surface of the first semi-circular portion faces an inner surface of the second semi-circular portion.

21. The intraluminal stent device of claim 1, wherein an inner surface of the first semi-circular portion faces an inner surface of the second semi-circular portion.

* * * * *